United States Patent
Carson et al.

(10) Patent No.: US 10,537,552 B2
(45) Date of Patent: Jan. 21, 2020

(54) SUBSTITUTED 5-HYDROXYOXINDOLES AND THEIR USE AS ANALGESICS AND FEVER REDUCERS

(71) Applicant: CARAFE DRUG INNOVATION, LLC, Monmouth Junction, NJ (US)

(72) Inventors: John R. Carson, Morristown, PA (US); Robert B. Raffa, Morristown, PA (US); Kenneth G. Carson, Princeton, NJ (US)

(73) Assignee: Carafe Drug Innovation, LLC, Monmouth Junction, NJ (US)

( * ) Notice: Subject to any disclaimer, the term of this patent is extended or adjusted under 35 U.S.C. 154(b) by 162 days.

(21) Appl. No.: 15/571,169

(22) PCT Filed: May 3, 2016

(86) PCT No.: PCT/US2016/030540
§ 371 (c)(1),
(2) Date: Nov. 1, 2017

(87) PCT Pub. No.: WO2016/179157
PCT Pub. Date: Nov. 10, 2016

(65) Prior Publication Data
US 2018/0256543 A1  Sep. 13, 2018

Related U.S. Application Data (60) Provisional application No. 62/157,092, filed on May 5, 2015.

(51) Int. Cl.
*A61K 31/404* (2006.01)
*A61P 29/02* (2006.01)
*A61K 45/06* (2006.01)

(52) U.S. Cl.
CPC ............ *A61K 31/404* (2013.01); *A61K 45/06* (2013.01); *A61P 29/02* (2018.01)

(58) Field of Classification Search
CPC .................................................. A61K 31/404
USPC ........................................................ 514/418
See application file for complete search history.

(56) References Cited

U.S. PATENT DOCUMENTS

| | | | |
|---|---|---|---|
| 3,751,417 A | 8/1973 | Allen, Jr. et al. | |
| 4,256,640 A | 3/1981 | Makisumi et al. | |
| 4,556,672 A | 12/1985 | Kadin | |
| 4,568,037 A | 2/1986 | Kawaguchi et al. | |
| 4,569,942 A | 2/1986 | Kadin | |
| 4,622,336 A | 11/1986 | Achini | |
| 4,665,194 A | 5/1987 | Crawford | |
| 4,678,802 A | 7/1987 | Kadin | |
| 4,690,943 A | 9/1987 | Kadin | |
| 4,721,712 A | 1/1988 | Kadin | |
| 4,725,616 A | 2/1988 | Kadin | |
| 5,783,575 A | 7/1998 | Jakobsen et al. | |
| 7,119,207 B2 | 10/2006 | O'Neill et al. | |
| 7,511,044 B2 | 3/2009 | Wang et al. | |
| 7,531,546 B2 | 5/2009 | Irie et al. | |
| 8,420,680 B2 | 4/2013 | Liotta et al. | |
| 8,722,670 B2 | 5/2014 | King et al. | |
| 2003/0105124 A1 | 6/2003 | Sobolov-Jaynes | |
| 2006/0247251 A1 | 11/2006 | Buxton et al. | |
| 2007/0072897 A1 | 3/2007 | Mahaney et al. | |

FOREIGN PATENT DOCUMENTS

| | | |
|---|---|---|
| CA | 1137489 A | 12/1982 |
| FR | 1657 M | 12/1961 |
| WO | WO 1997/038993 A1 | 10/1997 |
| WO | WO 2001/078722 A1 | 10/2001 |
| WO | WO 2007/091948 A2 | 8/2007 |
| WO | WO 2007/135527 A2 | 11/2007 |
| WO | WO 2012/025726 A1 | 3/2012 |

OTHER PUBLICATIONS

Childers et al., "Opiate Receptor Binding Affected Differentially by Opiates and Opioid Peptides," European Journal of Pharmacology, 1979, 55(1), 11-18.

Collier et al., "The Abdominal Constriction Response and its Suppression by Analgesic Drugs in the Mouse", British Journal of Pharmacology and Chemotherapy, 1968, 32(2), 295-310.

Combet-Farnoux, editor, European Journal of Medicinal Chemistry, Eur. J. Med. Chem—Chimica Therapeutica, Jan.-Feb. 1979, No. 1, 47-52.

(Continued)

*Primary Examiner* — Raymond J Henley, III
(74) *Attorney, Agent, or Firm* — BakerHostetler

(57) ABSTRACT

The present invention provides compounds and compositions which are useful in methods for modulating pain and fevers in a subject. These compounds are of the structure of formula (I), wherein Rx-R4, X, Y, and Z are defined herein, or a pharmaceutically acceptable salt, solvate, or prodrug thereof to the subject. In one embodiment, the compound is 5-hydroxy-7-methyloxindole.

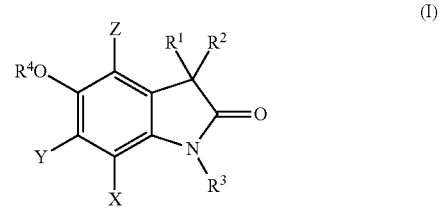

(I)

22 Claims, 4 Drawing Sheets

(56) References Cited

OTHER PUBLICATIONS

Crumeyrolle-Arias et al., "Inhibition of brain mitochrondrial monoamine oxidases by the endogenous compound 5-hydroxyoxindole", Biochemical Pharmacology, 2004, 67, 977-979.
Glaser et al., "Etodolac Selectively Inhibits Human Prostaglandin G/H Synthase 2 (PGHS-2) versus Human PGHS-1," European Journal of Pharmacology, 1995, 281(1), 107-111.
Itoh et al., "Introduction of a Hydroxy Group at the Para Position and N-Iodophenylation of N-Arylamides Using Phenyliodine (III) Bis(Trifluoroacetate)," The Journal of Organic Chemistry, 2002, 67(21), 7424-7428.
Luffy et al., "Morphine analgesia and tolerance in mice selectively bred for divergent swim stress-induced analgesia," European Journal of Pharmacology, 1994, 265(3), 171-174.
Papy-Garcia et al., "Detection and quantification of 5-hydroxyoxindole in mammalian sera and tissues by high performance liquid chromatography with multi-electrode electrochemical detection", Clinical Biochemistry, 2003, 36, 215-220.
Rajanarendar et al., "A facile synthesis, anti-inflammatory and analgesic activity of isoxazolyl-2,3-dihydrospiro[benzo[f]isoindole-1,3'-indoline]-2',4,9-triones," Bioorganic & Medicinal Chemistry Letters, 2013, 23(13), 3954-3958.
Takada et al., "Studies on Fused Indoles. II.[1)] Structural Modifications and Analgesic Activity of 4-Aminomethyltetrahydrothiopyrano[2,3-b]indoles", Chem Pharm. Bull., 1984, 32(3), 877-886.
Walker et al., "Substituted oxindoles. III. Synthesis and pharmacology of some substituted oxindoles", Journal of Medicinal Chemistry, 1970, 13(5), 983-985.
Walsh et al., "Antiinflammatory Agents, 3.[1] Synthesis and Pharmacological Evaluation of 2-Amino-3-benzoylphenylacetic Acid and Analogues," Journal of Medicinal Chemistry, 1984, 27(11), 1379-1388.

SUBSTITUTED 5-HYDROXYOXINDOLES AND THEIR USE AS ANALGESICS AND FEVER REDUCERS

CROSS-REFERENCE TO RELATED APPLICATIONS

This application is the National Stage Application of International Patent Application No. PCT/US2016/030540 filed May 3, 2016, which claims the benefit of the priority of U.S. Provisional Patent Application No. 62/157,092, filed May 5, 2015, of which both applications are incorporated by reference.

FIELD OF THE INVENTION

The disclosed invention is in the field of compounds for treating pain and reducing fever.

BACKGROUND

N-(4-Hydroxyphenyl)acetamide (acetaminophen, paracetamol, APAP) is a very widely used and effective pain relieving agent. It occupies a therapeutic niche between the highly efficacious opioid class and the non-steroidal anti-inflammatory drugs (NSAIDs, COX-1/COX-2). It lacks the typical side effects of the opioids (physical dependence, constipation, CNS) as well as the side effects associated with NSAIDs (gastrointestinal irritation, cardiovascular). Though lacking the efficacy of the opioids and the anti-inflammatory effects of NSAIDs, when used at recommended doses by appropriate subjects, acetaminophen would seem to be an almost side effect free pain relieving drug. The issue with acetaminophen is that, when used at high doses or in subjects with compromised liver function, it can cause liver damage. Furthermore, in conjunction with the high doses needed for pain relief, the potential toxicity also points to significant unmet medical need in terms of therapeutic index.

Even after over a century of use, there is no universally accepted mechanism. Mechanistic possibilities include interaction with the peroxidase site on the COX enzyme, action on the endocannabinoid system, indirect interaction with serotonergic pathways, action on TRP channels and indirect interaction with opioid pathways. Lack of certainty of acetaminophen's mechanism makes finding a safer alternative drug a challenge.

While the mechanism of action of acetaminophen remains unclear, the primary mechanism for its toxic effects is well understood. See, Scheme 1. At high doses, acetaminophen I undergoes oxidation to a reactive quinoneimine II which is able to react with tissue sulfhydryl groups (BioNuSH) to provide compound III with resulting cytotoxicity.

Scheme 1

Thus, there is a need for compounds for treating pain, while avoiding the toxic effects of acetaminophen. The invention is directed to these and other important needs.

SUMMARY

In one aspect, a method for treating pain in a subject is provided and includes administering an effective amount of a compound of the structure of formula (I), wherein $R^1$-$R^4$, X, Y, and Z are defined herein, or a pharmaceutically acceptable salt, solvate, or prodrug thereof to the subject.

In another aspect, a method for reducing fever in a subject is provided and includes administering an effective amount of a compound of the structure of formula (I), wherein $R^1$-$R^4$, X, Y, and Z are defined herein, or a pharmaceutically acceptable salt, solvate, or prodrug thereof to the subject.

In a further aspect, a composition is provided and contains (a) one or more pharmaceutically acceptable excipient; and (b) about 1000 mg or less of a compound of the structure of formula (I), wherein $R^1$-$R^4$, X, Y, and Z are defined herein, or a pharmaceutically acceptable salt, solvate, or prodrug thereof.

In yet another aspect, a kit is provided and contains (a) about 1000 mg or less of a compound of the structure of formula (I), wherein $R^1$-$R^4$, X, Y, and Z are defined herein, or a pharmaceutically acceptable salt, solvate, or prodrug thereof; and (b) instructions for administering the compound to a subject.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination. Further, reference to values stated in ranges includes each and every value within that range.

The inventors found that the compounds described herein are less likely cause an elevation of liver enzymes in a subject. The inventors also found that the compounds described herein do not bind significantly to the COX-1 and COX-2 receptors. It was also found that the compounds described herein do not bind significantly to the opioid receptor.

The fact that the compounds described herein had a therapeutic effect, but no minimal hepatotoxicity compared to acetaminophen was unexpected and unpredictable based on current assays. Specifically, since the mechanism of analgesic action of acetaminophen is unknown, prediction of in vivo activity based on an in vitro assay is not possible. Further, the separation of therapeutic and adverse effects of the compounds discussed herein is due to enhancing the separation between two distinct processes, i.e., analgesia (mechanism unknown) and hepatotoxicity (mechanism known), and thus not an obvious linear pathway. While these compounds were designed primarily to reduce toxicity due to the known metabolism mechanism, it was surprising that the biologic potency was enhanced in certain of the new compounds.

In addition to this surprising effect, it was found that the compounds discussed herein are more potent than acetaminophen. In one embodiment, the compounds discussed herein are at least about 1.5 times more potent than acetaminophen. In another embodiment, the compounds are at least about 2 times more potent than acetaminophen. In a further embodiment, the compounds are at least about 2.5 times more potent than acetaminophen. In still another embodiment, the compounds are at least about 3 times more potent than acetaminophen.

I. The Compounds

As discussed above, the compounds discussed herein have been found to have analgesic effects and effect reduction of fevers without having any of the dangerous side-effects of acetaminophen. These compounds are of the structure of formula (I):

(I)

In this structure, $R^1$ and $R^2$ are, independently, H, optionally substituted $C_1$ to $C_6$ alkyl, optionally substituted $C_3$ to $C_8$ cycloalkyl, optionally substituted $C_3$ to $C_8$ oxycycloalkyl, optionally substituted $C_1$ to $C_6$ hydroxyalkyl, $NH_2$, optionally substituted $C_1$ to $C_6$ alkylamino, optionally substituted $C_1$ to $C_6$ dialkylamino, OH, optionally substituted $C_1$ to $C_6$ alkoxy, optionally substituted $C_1$ to $C_6$ alkylcarboxy, optionally substituted $C_1$ to $C_3$ alkylidenecarboxy, optionally substituted $C_1$ to $C_6$ carbalkoxy, optionally substituted $C_1$ to $C_6$ alkylcarboxamido, N-(optionally substituted $C_1$ to $C_6$ alkyl)carboxamido, N,N-di(optionally substituted $C_1$ to $C_6$ alkyl)carboxamido, or optionally substituted $C_1$ to $C_6$ acyl. In one embodiment, $R^1$ is H. In another embodiment, $R^2$ is H. In a further embodiment, $R^1$ and $R^2$ are H. In yet another embodiment, the alkylidenecarboxy of $R^1$ and/or $R^2$ is methylidenecarboxy. Alternatively, $R^1$ and $R^2$ are joined to form a 3 to 7-membered ring.

$R^3$ is H, optionally substituted $C_1$ to $C_6$ alkyl, optionally substituted $C_1$ to $C_6$ acyl, N,N-(di-optionally substituted $C_1$ to $C_6$ alkyl)aminoacyl, optionally substituted $C_1$ to $C_6$ carbalkoxy, optionally substituted $C_1$ to $C_3$ phosphatoalkylenyl, or optionally substituted $C_1$ to $C_3$ acyloxyalkylenyl. In one embodiment, $R^3$ is H. In another embodiment, the phosphatoalkylenyl of $R^3$ is phosphatomethylenyl. In a further embodiment, the acyloxyalkylenyl of $R^3$ is acyloxymethylenyl.

$R^4$ is H, optionally substituted $C_1$ to $C_6$ alkyl, optionally substituted $C_1$ to $C_6$ acyl, N,N-(di-optionally substituted $C_1$ to $C_6$ alkyl)aminoacyl, N-(optionally substituted $C_1$ to $C_6$ alkyl)aminoacyl, $C_1$ to $C_6$ optionally substituted carbalkoxy, optionally substituted $C_1$ to $C_3$ phosphatoalkylenyl, amino ($C_3$ to $C_8$ optionally substituted cycloalkyl)acyl, or optionally substituted $C_1$ to $C_3$ acyloxyalkylenyl. In one embodiment, $R^4$ is H. In another embodiment, the phosphatoalkylenyl of $R^4$ is phosphatomethylenyl. In a further embodiment, the acyloxyalkylenyl of $R^4$ is acyloxymethylenyl.

X, Y and Z are, independently, H, optionally substituted $C_1$ to $C_6$ alkyl, optionally substituted $C_3$ to $C_8$ cycloalkyl, optionally substituted $C_1$ to $C_6$ hydroxyalkyl, optionally substituted $C_1$ to $C_6$ acyl, CN, halogen, $C_1$ to $C_3$ polyfluoroalkyl, $NO_2$, $NH_2$, optionally substituted $C_1$ to $C_6$ alkylamino, optionally substituted $C_1$ to $C_6$ dialkylamino, formyl, optionally substituted $C_1$ to $C_6$ carboxy, optionally substituted $C_1$ to $C_6$ carbalkoxy, OH, optionally substituted $C_1$ to $C_6$ alkoxy, or optionally substituted $C_1$ to $C_6$ thioalkoxy. In one embodiment, X is H. In another embodiment, X is $C_1$ to $C_6$ alkyl. In a further embodiment, Y is H. In still another embodiment, Z is H. In yet a further embodiment, Y and Z are H. In another embodiment, X, Y and Z are not all H. In a further embodiment, $R^1$-$R^3$, X, Y, and Z are not all H. Alternatively, any two or X, Y, and Z are joined to form a 3 to 7-membered ring.

In one embodiment, one or more hydrogen atom in the $R^1$-$R^4$, X, Y, and Z substituents may be replaced by a deuterium atom.

In one embodiment, the compound is 5-hydroxyindole, 5-hydroxy-7-methyloxindole, 5-hydroxy-7-ethyloxindole, 5-hydroxy-6-methyloxindole, 5-hydroxy-7-(2-propyl)oxindole, 5-hydroxy-7-bromo-oxindole, 4-methyl-5-hydroxy-oxindole, 4,6-dimethyl-5-hydroxy-oxindole, or a pharmaceutically acceptable salt, solvate, or prodrug thereof or 5-(N,N-diethylglycinyloxy)-7-methyloxindole hydrochloride salt.

The term "alkyl" as used herein refers to both straight- and branched-chain saturated aliphatic hydrocarbon groups. In one embodiment, an alkyl group has 1 to about 6 carbon atoms. In a further embodiment, an alkyl group has 1 to about 4 carbon atoms.

The term "cycloalkyl" as used herein refers to a cyclic, saturated aliphatic hydrocarbon group. The cycloalkyl may be a single ring or two or more rings fused together to form a multicyclic ring structure. A cycloalkyl group may thereby include a ring system having 1 to about 5 rings. In one embodiment, a cycloalkyl has 3 to about 14 carbon atoms. In another embodiment, a cycloalkyl has 3 to about 10 carbon atoms. In a further embodiment, a cycloalkyl has 3 to about 6 carbon atoms.

The term "alkoxy" as used herein refers to an O-(alkyl) group, where the point of attachment is through the oxygen-atom and the alkyl group is defined herein.

The term "halogen" as used herein refers to Cl, Br, F, or I.

The term "oxycycloalkyl" as used herein refers to a O-(cycloalkyl) group, where the point of attachment is through the oxygen-atom and the cycloalkyl group is defined herein.

The term "hydroxyalkyl" as used herein refers to a HO-(alkyl) group, where the point of attachment is through the oxygen-atom and the alkyl group is defined herein.

The term "acyl" as used herein refers to an (alkyl)C(O)— group, where the point of attachment is through the carbon-atom of the carbonyl and the alkyl group is defined herein.

The term "acyloxyalkylenyl" as used herein refers to the (alkyl)C(O)O(alkyl)- group, where the point of attachment is through a carbon-atom of one alkyl group and both alkyl group are, independently, defined herein.

The term "alkylamino" as used herein refers to the (alkyl)NH— group, where the point of attachment is through the nitrogen-atom and the alkyl group is defined herein. Similarly, the term "dialkylamino" refers to the —N(alkyl)$_2$ group, where the point of attachment is through the nitrogen-atom and each alkyl group is, independently, defined herein.

The term "alkylcarboxamido" as used herein refers to an (alkyl)NHC(O)— group, where the point of attachment is through the carbon-atom and the alkyl group is defined herein.

The term "amino(cycloalkyl)acyl" as used herein refers to a (cycloalkyl) NH(alkyl)C(O)— group, where the point of attachment is through the carbon-atom and the alkyl and cycloalkyl groups are defined herein.

The term "alkylcarboxy" as used herein refers to -(alkyl)C(O)OH, where the point of attachment is through a carbon-atom of the alkyl and the alkyl group is defined herein.

The term "alkylidenecarboxy" as used herein refers to a=CHC(O)OH group, where the point of attachment is a double bond through the carbon-atom.

The term "carbalkoxy" as used herein refers to the —C(O)O(alkyl) group, where the point of attachment is through the carbon-atom and the alkyl group is defined herein.

The term "carboxy" as used herein refers to a —C(O)OH, where the point of attachment is through the carbon-atom.

The term "N-(alkyl)aminoacyl" as used herein refers to an (alkyl)NH(alkyl)C(O)— group, where the point of attachment is through the carbon-atom and the alkyl groups are independently defined herein. Similarly, the term "N,N-(di-alkyl)aminoacyl" refers to the (alkyl)N(alkyl)$_2$C(O)— group, where the point of attachment is through the carbon-atom and the alkyl groups are independently defined herein.

The term "N-(alkyl)carboxamido" as used herein refers to an (alkyl)NHC(O)— group, where the point of attachment is through a carbon-atom and the alkyl group is defined herein. Similarly, the term "N,N-(di-alkyl)carboxamido" refers to an (alkyl)$_2$NC(O)— group, where the point of attachment is through the carbon-atom and the alkyl groups are independently defined herein.

The term "phosphatoalkylenyl" as used herein refers to an -(alkyl)-O—P(O)$_3$ group, where the point of attachment is through a carbon-atom of the alkyl group and the alkyl group is defined herein.

The term "thioalkoxy" as used herein refers to an (alkyl)S— group, where the point of attachment is through the sulfur-atom and the alkyl group is defined herein.

The term "3 to 7-membered ring" as used herein refers to a carbon-based ring, which may be unsaturated or saturated. The ring may also include one or more heteroatoms in the backbone of the ring, provided that such the resultant ring is stable. In one embodiment, the ring may include one or more, i.e., 1, 2, 3, 4, or 5, oxygen, sulfur, or nitrogen heteroatoms. The carbon and/or heteroatoms of the ring may also be substituted, as their valency will permit, by one or more groups recited herein. In one embodiment, the ring is a cycloalkyl as defined above. In another embodiment, the ring is a heteroaryl ring. In a further embodiment, the ring is a heterocycle. In yet another embodiment, the ring is a phenyl group optionally substituted with one or more group as presented herein.

The term "heteroaryl" as used herein refers to a monocyclic, bicyclic, or polycyclic aromatic ring system containing at least one oxygen, sulfur and nitrogen in the backbone of the ring. Examples of heteroaryl groups include, without limitation, furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline.

The term "heterocycle" as used herein refers to monocyclic, bicyclic, polycyclic, or bridged head molecule having at least heteroatom in the backbone of the ring. The heterocycle may be saturated or partially saturated. Examples of heterocycles include, without limitation, aziridine, oxirane, oxirene, thiirane, pyrrolidine, pyrrolidine, dihydrofuran, tetrahydrofuran, dihydrothiophene, tetrahydrothiophene, dithiolane, piperidine, tetrahydropyridin-1-yl, tetrahydropyran, pyran, thiane, thiine, piperazine, azepane, diazepane, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6 azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane.

The term "substituted" as used herein refers to the substituent of an atom or moiety for another atom of moiety, provided that the substitution results in a stable chemical compound, as determined by those skilled in the art. In one embodiment, the substituent is an alkyl, cycloalkyl, alkoxy, halogen, oxycycloalkyl, hydroxyalkyl, acyl, acyloxyalkylenyl, alkylamino, alkylcarboxamido, amino(cycloalkyl)acyl, alkylcarboxy, alkylidenecarboxy, carbalkoxy, carboxy, N-(alkyl)aminoacyl, N,N-(di-alkyl)aminoacyl, N-(alkyl)carboxamido, N,N-(di-alkyl)carboxamido, phosphatoalkylenyl, thioalkoxy, phenyl, heterocycle, or heteroaryl.

(i) Salts

The compounds discussed above may be used in the form of salts derived from pharmaceutically or physiologically acceptable acids, bases, alkali metals and alkaline earth metals.

Pharmaceutically acceptable acid salts may be formed from organic and inorganic acids. Examples of acids include acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, among others. Accordingly, the salts described herein contain the counterions of these acids.

Pharmaceutically acceptable basic salts may also be formed from inorganic or organic bases. In one embodiment, the basic salt contains an ammonium, alkali metal, or alkaline earth counterion. Examples of inorganic bases include, without limitation, sodium hydroxide, potassium hydroxide, calcium hydroxide, and magnesium hydroxide. Examples of organic bases include, without limitation, ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, diethanolamine, or ethylenediamine.

(ii) Prodrugs

The salts, as well as other compounds, can be in the form of a compound which, when administered in such form, converts to the active moiety in vivo. In one embodiment, the prodrug is an ester, carbamate, optionally substituted $C_1$ to $C_3$ phosphatoalkylenyl, optionally substituted $C_1$ to $C_3$ acyloxyalkylenyl, or alkyloxymethyleneoxy bearing a water solubilizing group.

The term "water solubilizing group" as used herein refers to a chemical moiety which enhances the water-solubility of the compound. One of skill in the art would be able to select a water solubilizing group for use herein. In one embodiment, the prodrug contains a water solubilizing group including an amino, alkylamino, dialkylamino, carboxy, or phosphato group. In another embodiment, the prodrug contains a phosphatoalkylenyl group such as phosphatomethylenyl.

While shown without respect to stereochemistry below, the compounds may be optical isomers and diastereoisomers and racemic and resolved, enantiomerically pure R and S stereoisomers. In one embodiment, the compound is a single enantiomer. In another embodiment, the compound is a mixture of R and S stereoisomers.

II. Compositions Containing the Compounds

Pharmaceutical compositions contain a compound discussed herein in a pharmaceutically acceptable carrier with other optional suitable pharmaceutically inert or inactive ingredients. In one embodiment, a compound of formula (I) is combined with one or more pharmaceutically acceptable excipient. In another embodiment, a compound of formula (I) is combined with one or more water-soluble pharmaceutically acceptable excipient.

The pharmaceutical compositions include a compound described herein formulated neat or with one or more pharmaceutical carriers or excipients for administration. Such carriers or excipients are chosen by those skilled in the art based on the solubility and chemical nature of the compound, chosen route of administration, among others. The pharmaceutical carrier may be solid or liquid.

Examples of excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, buffer, preservatives, solubilizers, sorbents, stabilizers, sweeteners, surfactants, suspending agents, syrups, thickening agents, or viscosity regulators. See, the excipients described in the "Handbook of Pharmaceutical Excipients", 5th Edition, Eds.: Rowe, Sheskey, and Owen, APhA Publications (Washington, D.C.), Dec. 14, 2005, which is incorporated herein by reference.

Liquid carriers are typically utilized in preparing solutions, suspensions, emulsions, syrups and elixirs. In one embodiment, the compound is dissolved or suspended in a liquid carrier. In another embodiment, the liquid carrier is sterile. In a further embodiment, the liquid carrier includes, without limitation, water, organic solvents, oils, fats, or any combinations thereof. In yet another embodiment, the liquid carrier is a water-soluble organic solvent. In still a further embodiment, the liquid carrier is dimethylsulfoxide, alcohols such as monohydric alcohols and polyhydric alcohols, e.g., glycols and their derivatives such as polyethylene glycol 300, polyethylene glycol 400, ethanol, propylene glycol, glycerin, N-methyl-2-pyrrolidone, dimethylacetamide, among others. Oils may be utilized as the liquid carrier and may be selected from, without limitation, coconut oil, *arachis* oil, corn oil, peanut oil, and sesame oil and oily esters such as ethyl oleate isopropyl myristate. The carrier may also be an organic liquid/semi-solid including, without limitation, beeswax, d-α-tocopherol, oleic acid, medium-chain mono- and diglycerides, sulfobutylether-3-cyclodextrin, and phospholipids (hydrogenated soy phosphatidylcholine, distearoylphosphatidylglycerol, L-α-dimyristoylphosphatidylcholine, L-α-dimyristoylphosphatidylglycerol). Non-ionic surfactants may be utilized as the carrier and include polyethoxylated castor oils, d-α-tocopherol polyethylene glycol 1000 succinate, polyoxyethylene ester of 12-hydroxystearic acid, sorbitan monooleate, poloxamers, olelyl and linoleoyl macrogol-6 glycerides, lauroyl macrogol glycerides, and mono- and di-fatty acid esters of PEG 300, 400, or 1750, among others.

Alternatively, the compound may be formulated in a solid carrier. In one embodiment, the composition may be compacted into a unit dose form, i.e., tablet or caplet. In another embodiment, the composition may be added to unit dose form, i.e., a capsule in soft or hard form such as a gelatin, hydroxypropylmethylcellulose or polyvinylalcohol capsule. In a further embodiment, the composition may be formulated for administration as a powder. The solid carrier may perform a variety of functions, i.e., may perform the functions of two or more of the excipients described above. In one embodiment, the solid carrier is, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidone, low melting waxes, ion exchange resins, and kaolin. The solid carrier can contain other suitable excipients, including those described herein.

In one embodiment, the excipient is one or more of a polyethylene glycol, polyvinylpyrrolidone, PEG-8 caprylic/capric glycerides, cyclodextrin (α-cyclodextrin, β-cyclodextrin, hydroxypropyl-β-cyclodextrin), polysorbate (20 or 80), carboxymethylcellulose, hydroxypropylcellulose, or any combinations thereof.

The compositions discussed herein may also include one or more opiate. The opiate may be a natural opiate, an ester of a morphine opiate, a semi-synthetic opiate, a fully synthetic opiate, or an endogenous opioid peptide. In one embodiment, the opiate is a natural opiate including, without limitation, alkaloids contained in the resin of the opium poppy, codeine, thebaine, leaves from *Mitragyna speciosa*, Salvinorin A, or any combinations thereof. In another embodiment, the opiate is an ester of a morphine opiate including, without limitation, diacetylmorphine, nicomorphine, dipropanoylmorphine, desomorphine, dibenzoylmorphine, diacetyldihydromorphine, or any combinations thereof. In a further embodiment, the opiate is a semi-synthetic opioids including, without limitation, hydromorphone, hydrocodone, oxycodone, oxymorphone, ethylmorphine, buprenorphine, or any combinations thereof. In yet another embodiment, the opiate is a fully synthetic opioids including, without limitation, fentanyl, pethidine, levorphanol, methadone, tramadol and dextropropoxyphene. In still another embodiment, the opiate is an endogenous opioid peptide including, without limitation, endorphins, enkephalins, dynorphins, endomorphins, morphine, or any combinations thereof. One of skill in the art would readily be able to determine the amount of opiate to be administered to the patent.

III. Methods of Using the Compounds or Compositions

As discussed above, the compounds and compositions described herein may be used in a variety of methods for treating a subject. In one embodiment, the compounds and compositions may be used in treating pain in a subject. In another embodiment, the compounds and compositions may be used in reducing a fever in a subject.

Advantageously, the compounds and compositions described herein do not function through the COX-1 receptor, COX-2 receptor, opioid or any combinations thereof. Accordingly, side effects, such as non-steroidal anti-inflammatory drug (NSAID) or opioid side effects, associated with these receptors are not exhibited by the subject. In one embodiment, administration of the compounds or compositions described herein does not result in NSAID side effects such as gastrointestinal irritation, cardiovascular effects, or any combinations thereof. In another embodiment, administration of the compounds or compositions described herein does not result in opioid side effects such as physical drug dependence, constipation, CNS, or a combination thereof. In another embodiment, administration of the compounds or compositions described herein does not result in liver-related side effects.

The inventors also found that the compositions discussed herein and compositions containing same do not cause liver damage in a subject. In one embodiment, toxic metabolites are not formed upon administration of the compounds discussed herein. In a further embodiment, a toxic metabolite analogous to the toxic metabolite produced by high doses of acetaminophen is not formed in the subject/patient.

The term "patient" or "subject" as used herein refers to a mammalian animal. In one embodiment, the patient or subject is a human. In another embodiment, the patient or subject is a veterinary or farm animal, a domestic animal or pet, or animal normally used for clinical research. The patient or subject may be a child, teenager, or adult (mature or elderly).

As used herein, "treatment" encompasses treatment of a subject clinically diagnosed as having a disease or medical condition. In one embodiment, the subject is treated and the disease is eradicated, i.e., the subject is cured or goes into remission.

As described herein, an effective amount of a compound is that amount of a compound which reduces pain or a fever for a subject. The effective amount of the compound may vary and depend upon the formulation and route of delivery. Accordingly, the effective amount may be varied as determined by the attending physician and calculated on a single or daily dosage. The particular dosage utilized may depend on a number of factors including, without limitation, the specific cognitive deficit and the size, age and response pattern of the subject. The effective amount may be provided on an irregular or regular schedule, i.e., daily, weekly, monthly, or yearly basis. In one embodiment, the effective amount of a single dose of the compound is about 1000 mg or less, i.e., about 1000, 950, 900, 850, 800, 750, 700, 650, 600, 550, 500, 450, 400, 350, 300, 250, 200, 150, 100, 50, 25, 20, 15, 10, 5, 1, 0.5, 0.25, 0.1 mg, or less. In another embodiment, the effective amount of a daily dosage is about 200 mg or less, i.e., about 2000, 1950, 1900, 1850, 1800, 1750, 1700, 1650, 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, 150, 100, 50, 25, 20, 15, 10, 5, 1, 0.5, 0.25, 0.1 mg, or less.

In one embodiment, the effective amount for the first dose of the compound may be higher than the effective amount for one or more of the subsequent doses. In another embodiment, the effective amount for the first dose of the compound may be lower than the effective amount for one or more of the subsequent doses.

The compound or composition may be administered to a subject by any desirable route, taking into consideration the specific condition for which it has been selected. The compound may, therefore, be delivered orally, by injection, inhalation, ocularly, transdermally, intravascularly, cutaneously, subcutaneously, intramuscularly, sublingually, intracranially, epidurally, rectally, intravesically, vaginally, or any combination thereof.

IV. Kits Containing the Compounds

Also provided herein are kits of pharmaceutical formulations containing a compound of formula (I) or composition described herein. The kits may be organized to indicate a single formulation or combination of formulations. The composition may be sub-divided to contain appropriate quantities of the compound. The unit dosage can be packaged compositions such as packeted powders, vials, ampoules, prefilled syringes or sachets containing liquids.

The compound or composition described herein may be a single dose or for continuous or periodic discontinuous administration. For continuous administration, a kit may include the compound in each dosage unit. For periodic discontinuation, the kit may include placebos during periods when the compound is not delivered. When varying concentrations of the composition, the components of the composition, or relative ratios of the compound or other agents within a composition over time is desired, a kit may contain a sequence of dosage units.

The kit may contain packaging or a container with the compound formulated for the desired delivery route. The kit may also contain dosing instructions, an insert regarding the compound, instructions for monitoring circulating levels of the compound, or combinations thereof. Materials for performing using the compound may further be included and include, without limitation, reagents, well plates, containers, markers or labels, and the like. Such kits are packaged in a manner suitable for treatment of a desired indication. Other suitable components to include in such kits will be readily apparent to one of skill in the art, taking into consideration the desired indication and the delivery route. The kits also may include, or be packaged with, instruments for assisting with the injection/administration or placement of the compound within the body of the subject. Such instruments include, without limitation, an inhalant, syringe, pipette, forceps, measuring spoon, eye dropper or any such medically approved delivery means. Other instrumentation may include a device that permits reading or monitoring reactions in vitro.

The compound or composition of these kits also may be provided in dried, lyophilized, or liquid forms. When reagents or components are provided as a dried form, reconstitution generally is by the addition of a solvent. The solvent may be provided in another packaging means and may be selected by one skilled in the art.

A number of packages or kits are known to those skilled in the art for dispensing pharmaceutical agents. In one embodiment, the package is a labeled blister package, dial dispenser package, or bottle.

In one embodiment, a kit is provided and contains (a) about 1000 mg or less of a compound of the structure of formula (I) and (b) instructions for administering said compound to a subject.

EXAMPLES

Chemical shifts for NMR data are reported in parts per million (ppm) relative to tetramethylsilane in d-units, and coupling constants (J-values) are given in hertz (Hz). Data are reported in the following format: chemical shift, multiplicity, coupling constants, and assignment. Reactions were monitored by TLC using 0.25 mm E. Merck silica gel plates (60 $F_{254}$) and were visualized with UV light. Analytical HPLC spectra were collected on reverse-phase HPLC systems equipped with a UV detector measuring absorbance at 220 nm and a mass detector using electrospray ionization. HPLC/MS was performed using a gradient of 10% acetonitrile:water (both 0.1% TFA) to 90% acetonitrile:water over 15 minutes at 1 mL/min on a Waters Symmetry™ C-18 column (3.5μ, 4.6×75 mm reverse phase column).

Example 1: Preparation of 5-Hydroxy-7-methyloxindole

The title compound may be purchased from WuXu App Tech (catalog #AM802907, CAS #1082041-62-0) or prepared using the following synthetic routes. The following spectral data was obtained for this compound: $^1$H NMR (400 MHz, methanol-$d_4$) δ ppm 6.55 (s, 1H), 6.46 (s, 1H), 3.43 (s, 2H), 2.17 (s, 3H). HPLC retention time: 1.91 minutes. MS (ESI) m/z: 164.1 (m+1).

The title compound may also be prepared by making the transformations described in Scheme 2. Specifically, 5-methoxy-7-methyloxindole was prepared as described in U.S. Pat. No. 4,622,336 and reacted with boron tribromide according to the procedure described in International Patent Publication No. WO-2012/025726 in the preparation of 1,3-dihydro-5-hydroxy-2H-indol-2-one from 1,3-dihydro-5-methoxy-2H-indol-2-one. $^1$H NMR (400 MHz, methanol-$d_4$): δ 6.55 (s, 1H), 6.46 (s, 1H), 3.43 (s, 2H), and 2.17 (s, 3H). HPLC retention time: 1.91 minutes. MS (ESI) m/z: 164.1 (M+1).

Scheme 2

-continued

Example 2: Preparation of 5-Hydroxy-7-ethyloxindole

The title compound was prepared using the methods described in Itoh, Journal of Organic Chemistry, 67(21): 7424; (2002), which is incorporated by reference. Specifically, 7-ethyloxindole was reacted with phenyliodine(III) bis(trifluoroacetate) to form the product. See. Scheme 3. $^1$H NMR (400 MHz, DMSO-$d_6$) δ ppm 10.05 (s, 1H), 8.78 (br s, 1H), 6.55 (s, 1H), 6.43 (s, 1H), 3.35 (s, 2H), 2.45 (m, 2H), and 1.05 (t, 3H). HPLC retention time: 2.39 minutes. MS (ESI) m/z: 178.2 (M+1).

Example 3: Preparation of 5-Hydroxy-6-methyloxindole

The title compound was prepared using the methods described in Itoh cited above. Specifically, 6-methyloxindole was reacted with phenyliodine(III) bis(trifluoroacetate) to form the product. See, Scheme 4. $^1$H NMR (400 MHz, DMSO-$d_6$) δ ppm 10.02 (s, 1H), 8.78 (s, 1H), 6.55 (s, 1H), 6.43 (s, 1H), 3.45 (s, 2H), and 2.05 (s, 3H). HPLC retention time: 2.12 minutes. MS (ESI) m/z: 164.1 (M+1).

Example 4: Preparation of 5-Hydroxy-7-(2-isopropyl)oxindole

The title compound was prepared using the methods described in Itoh cited above. Specifically, 7-(2-propyl) oxindole was reacted with phenyliodine(III) bis(trifluoroacetate) to form the product. See, Scheme 5. $^1$H NMR (400 MHz, methanol-$d_4$) δ ppm 6.38 (s, 2H), 3.45 (s, 2H), 2.92 (m, 1H), and 1.23 (d, 6H). HPLC retention time: 2.76 minutes. MS (ESI) m/z: 192.2 (M+1).

Example 5: Preparation of 5-Hydroxy-7-bromo-oxindole

The title compound was prepared using the methods described in Itoh cited above. Specifically, 7-bromo-oxindole was reacted with phenyliodine(III) bis(trifluoroacetate) to form the product. See, Scheme 6.

Example 6: Preparation of 4-Methyl-5-hydroxy-oxindole

The title compound is prepared using the methods described in Itoh cited above. Specifically, 4-methyl-oxindole is reacted with phenyliodine(III) bis(trifluoroacetate) to form the product. See, Scheme 7.

Scheme 7

Example 7: Preparation of 4,6-Dimethyl-5-hydroxy-oxindole

The title compound is prepared using the methods described in Itoh cited above. Specifically, 4,6-dimethyl-oxindole is reacted with phenyliodine(III) bis(trifluoroacetate) to form the product. See, Scheme 8.

Scheme 8

Example 8: Preparation of 5-(N,N-Diethylglycinyloxy)-7-Methyloxindole hydrochloride salt A solution of 5-hydroxy-7-methyloxindole in pyridine is treated with dicyclohexyl carbodiimide and N,N-diethyl glycine to provide the title compound. $^1$H NMR (400 MHz, methanol-$d_4$) δ ppm 6.97 (s, 1H), 6.90 (s, 1H), 4.45 (s, 2H), 3.4-3.3 (m, 5H), 3.55 (s, 1H), 2.26 (s, 3H), and 1.39 (t, J=7.3 Hz, 6H). HPLC retention time: 2.08 minutes. MS (ESI) m/z: 277 (M+1).

Example 9: Efficacy of 5-hydroxyoxindole

A. Measure of Efficacy

The example was performed to compare the antinociception (animal equivalent of analgesia) produced by the oral administration of 5-hydroxyoxindole vs acetaminophen in a standard model in mice.

B. Animals

Male B6C3F1 mice (Taconic), 8-10 weeks of age were utilized. The mice were received at the facility at least one week prior to testing and housed in standard polycarbonate cages with filter tops. The experiments were done in accordance with the guidelines of the National Institutes of Health (NIH) and with the guidelines of the Committee for Research and Ethical Issues of the IASP (International Association for the Study of Pain) and were approved by the Institutional Animal Care and Use Committee (IACUC) of Taconic Laboratories. Four or five animals were housed per cage and food and water were provided ad libitum. Prior to initiation of the study, the mice were examined to assure adequate health and suitability. They were maintained on a 12 h/12 h light/dark cycle and room temperature was maintained between 20 and 23° C. with a relative humidity maintained between 30 and 70%. All compounds were tested in naïve animals.

C. Drug Treatment

All compounds were administered orally 10 mL/kg, with a 30 minute pretreatment time. Each compound was dissolved in DMSO as a stock solution and mixed with methylcellulose (2%) before testing. Each compound was initially tested in five mice at a dose of 300 mg/kg in the abdominal constriction response test (Collier, British Journal of Pharmacology and Chemotherapy 32(2): 295-310, 1968). Based upon the results of the initial test, the dose-response relationship for each active compound was determined by measuring the level of analgesia produced by at least 3 escalating doses of the test compound. The measurement of inhibition of abdominal constriction for acetaminophen was repeated using 6% Tween® 20 reagent as the vehicle. In this case, both compounds were clearly in suspension when administered to the animals.

D. Assessment of Analgesia

A modified version of the standard abdominal constriction response test (Collier cited above) was used to assess antinociception (analgesia). Mice were habituated for 1 h in a transparent test box (5×5×10 inches) before injections. Vehicle or test compound was administered p.o. (per os) 30 min prior to an intraperitoneal (i.p.) injection of 0.9% acetic acid (10 mL/kg) and the number of responses (stretching of the hind limbs accompanied by a contraction of the abdominal muscles) to the acetic acid injection were counted over the subsequent 30 min period. The mice from each cage were randomly assigned to the dosing groups and the mice from each group were injected in a random order.

E. Data Analysis

One-way ANOVA was used to determine significant difference from the vehicle control-treated animals. Dose response data was fit by non-linear regression analysis to a logit model to provide an estimate of the $ED_{50}$ value.

F. Results

Figure 1:
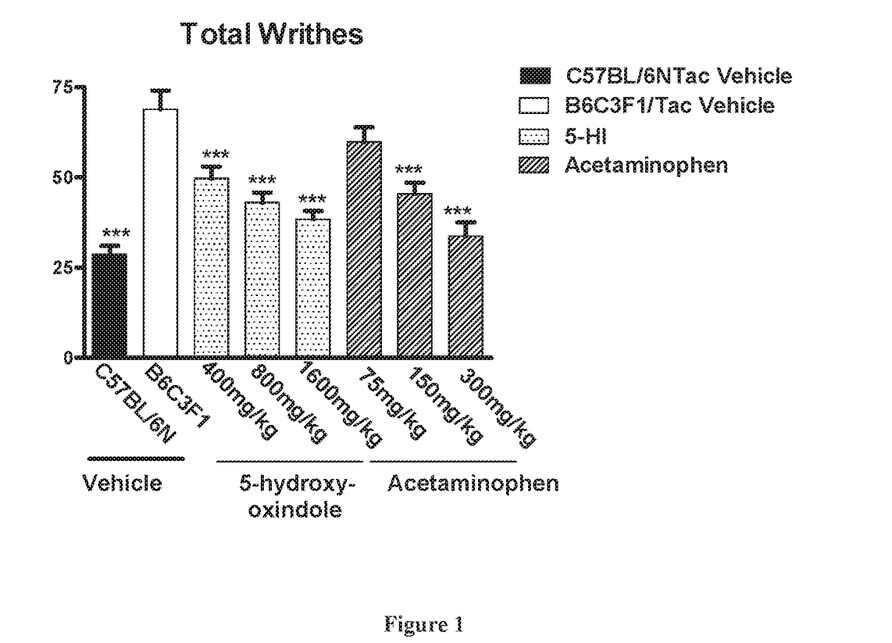
FIG. 1 is a bar graph illustrating the effects of control vehicle C57BL/6N (■ bar), G6C3F1 (□ bar), acetaminophen (▦ bar) at concentrations of 400, 800, and 1600 mg/kg and 5-hydroxyindole (5-HI; ▨ bar) at concentrations of 75, 150, and 500 mg/kg in B6C3F1 Mice. ***P<0.001; ANOVA with Dunnett's post hoc compared to Vehicle control B6C3F1/Tac.

See FIG. 1 below.

The study was carried out in B6C3F1 mice, and was a comparison of acetaminophen with known analgesic 5-hydroxyoxindole (5-HI). Acetaminophen produced a robust and dose-related inhibition of acetic acid-induced behavioral response in the dose range from 75 to 300 mg/kg (FIG. 1), which is consistent with literature reports of acetaminophen's activity in this assay. Known compound 5-hydroxoxindole (5-HI) also produced a statistically significant, dose-related inhibition of acetic acid-induced response (FIG. 1). Note that higher doses of 5-HI were required to cause the same analgesic efficacy as that seen with acetaminophen.

Example 10: Efficacy of 5-hydroxy-7-methyloxindole Compared to Acetaminophen This example compares the antinociception (animal equivalent of analgesia) produced by the oral administration of 5-hydroxy-7-methyloxindole vs. acetaminophen. Initial studies were performed using 10% DMSO/Cremophor™ as the vehicle. To enable a comparison with other datasets, 5-hydroxy-7-methyloxindole was subsequently tested using 6% Tween 20® reagent as the vehicle.

A. Animals

Male C57/B16 mice (Taconic), 8 weeks of age, were used in this study. The mice were received at Drexel University at least one week prior to testing and housed in standard polycarbonate cages with filter tops. Experiments were done in accordance with the guidelines of the National Institutes of Health and with the guidelines of the Committee for Research and Ethical Issues of IASP and were approved by the Animal Care and Use Committee of Drexel University College of Medicine. Four to five animals were housed per cage and food and water were provided ad libitum. Prior to initiation of the study, the animals were examined to assure adequate health and suitability. Mice were maintained on a 12/12 light/dark cycle and room temperature was maintained between 20 and 23° C. with a relative humidity maintained between 30% and 70%.

B. Drug Treatment

Compounds were administered orally 10 mL/kg, with a 30 minute pretreatment time. All compounds were tested in naïve animals. All compounds were administered orally 10 mL/kg, with a 30 minute pretreatment time. Each compound was dissolved in DMSO as a stock solution and mixed with Cremophor™ (1:1 v/v) before testing. The mixed solutions were diluted 1:4 with sterile water (the final concentration of DMSO/Cremophor™ reagent was 10%) immediately before administration to maximize the amount of compound in solution and improve the uniformity of any compound substance remaining in suspension. It is possible that some of the drug was in suspension at the time of administration. Each compound was initially tested in 5 mice at a dose of 300 mg/kg in the writhing test to assess their ability to alleviate abdominal pain. Based on the results of the initial test, the dose-response relationship for each active compound was determined by measuring the level of analgesia produced by at least 3 escalating doses of the test compound. The measurement of inhibition of writhing for acetaminophen and 5-hydroxy-7-methyloxindole were repeated using 6% Tween® 20 reagent as the vehicle. In this case, both compounds were clearly in suspension when administered to the animals.

C. Assessment of Analgesia

A modified version of the standard abdominal irritant test was used to assess analgesia. Mice were habituated for 1 h in a transparent test box (5×5×10 inches) before any injections. Vehicle or test compound was administered p.o. (per os) 30 min prior to an intraperitoneal (i.p.) injection of 0.6% acetic acid (10 mL/kg) and the number of writhing responses (stretching of the hind limbs accompanied by a contraction of the abdominal muscles) to the acetic acid injection were counted over the subsequent 30 min period. The mice from each cage were randomly assigned to the dosing groups and the mice from each group were injected in a random order.

D. Data Analysis

The one-way ANOVA was used to determine significant difference from the vehicle control treated animal. Dose response data for 5-hydroxy-7-methyloxindole was fit by non-linear regression analysis to a logit model to provide an estimate of $ED_{50}$.

E. Results

Figure 2:
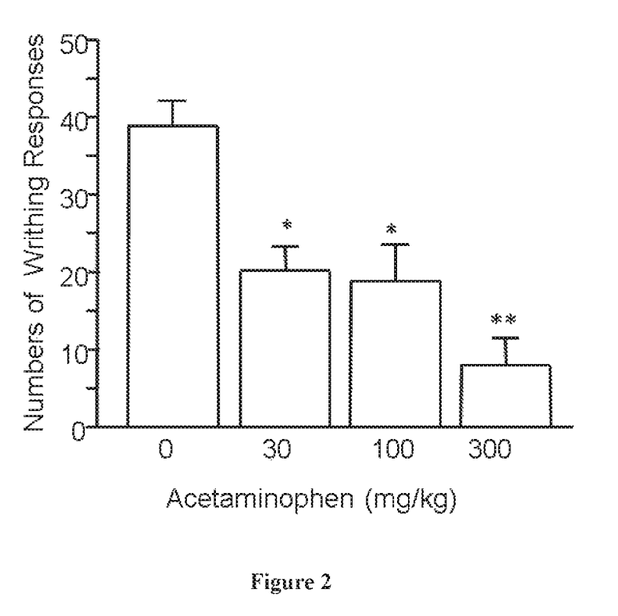
FIG. 2 is a bar graph illustrating the effect of acetaminophen alone at 0, 30, 100, and 300 mg/kg as a factor of the number of writhing responses. *p<0.05; **p<0.01 compared to vehicle control (dose=0) by one-way ANOVA.

Acetaminophen produced a robust and dose-related inhibition of acetic acid-induced behavioral response in the dose range from 30 to 300 mg/kg, which is consistent with literature reports of acetaminophen's activity in this assay, and roughly consistent with the previous study. See FIG. 2 below.

Figure 3:
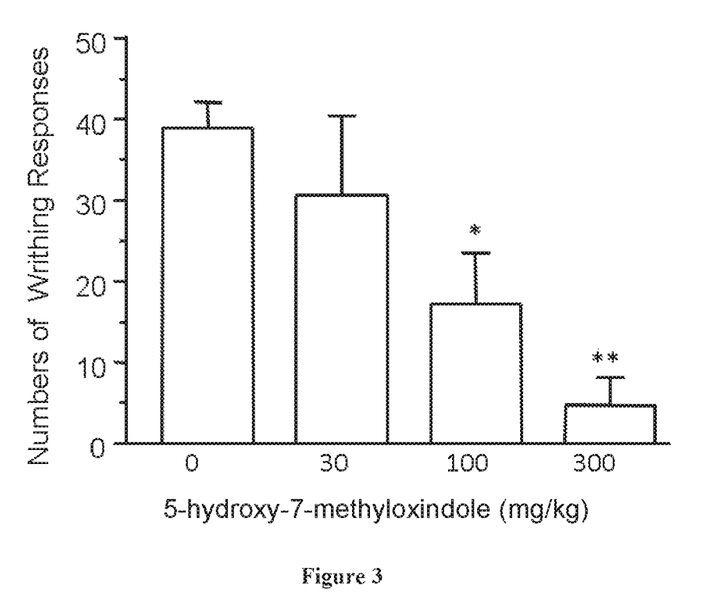
FIG. 3 is a bar graph illustrating the effect of 5-hydroxy-7-methyloxindole as a factor of the number of writhing responses. *p<0.05 and **p<0.01 compared to vehicle control (dose=0) by one-way ANOVA.
Figure 4:
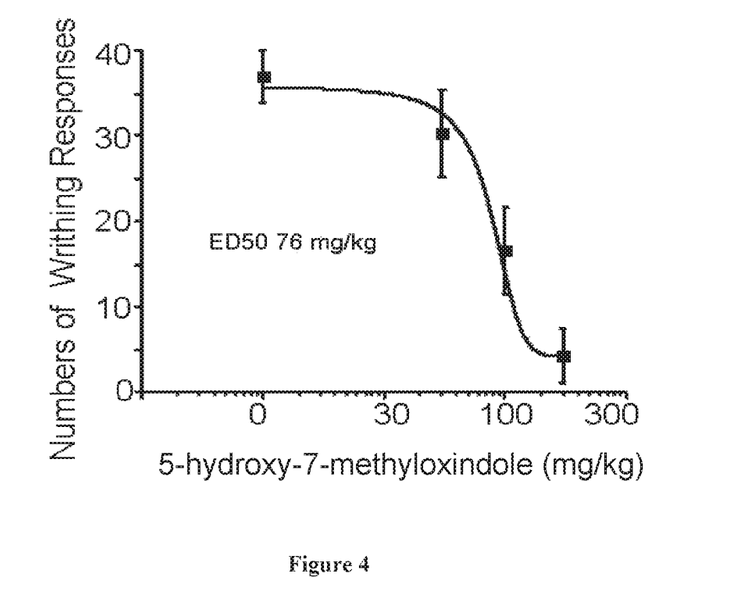
FIG. 4 is a dose-response curve for 0, 30, 100, and 300 mg/kg concentrations of 5-hydroxy-7-methyloxindole vs. the number of writhing responses.

5-Hydroxy-7-methyloxindole also produced a robust and dose-related inhibition of acetic acid-induced response (FIG. 3). Fitting the dose-response data to a logit model yielded an estimate of the $ED_{50}$ value of 76 mg/kg (FIG. 4).

Figure 5:
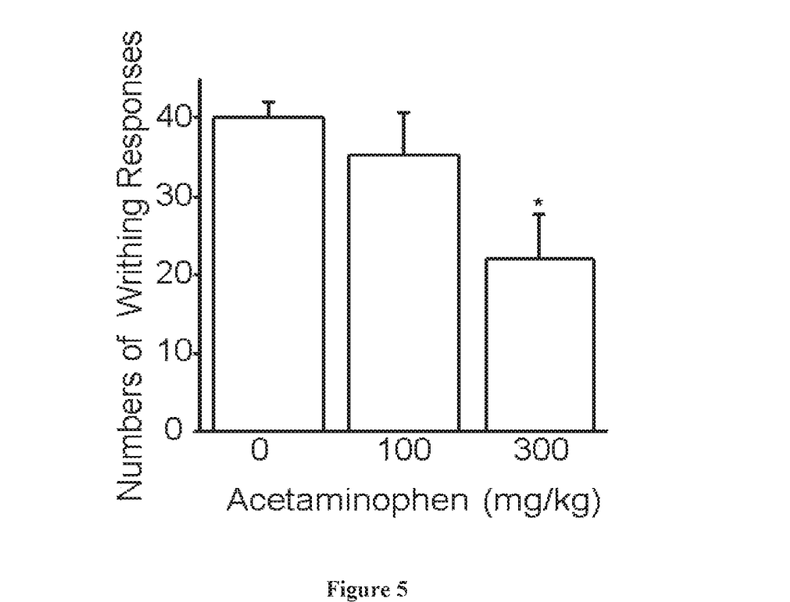
FIG. 5 is a bar graph illustrating the effect of acetaminophen in 6% Tween® 20 reagent for concentrations 0, 100, and 300 mg/kg concentrations on the number of writhing responses. *p<0.05 compared to vehicle control (dose=0) by one-way ANOVA.
Figure 6:
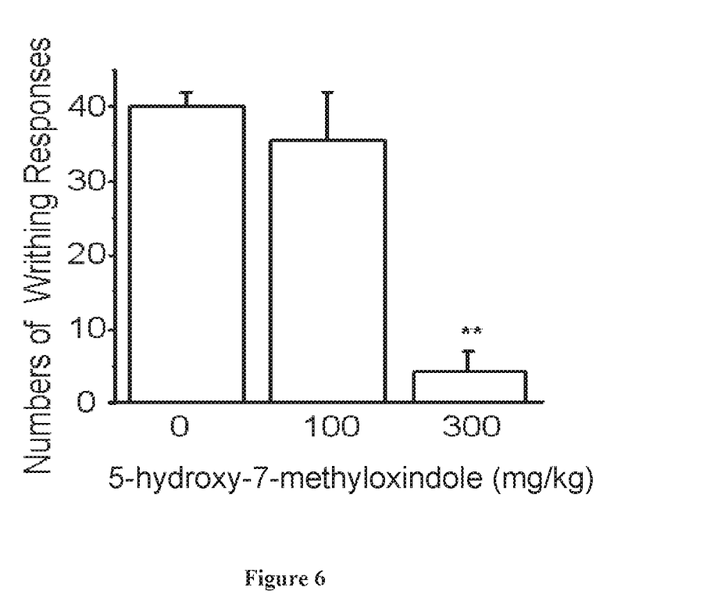
FIG. 6 is a dose-response for 0, 100, and 300 mg/kg concentrations of 5-hydroxy-7-methyloxindole in 6% Tween® 20 reagent on the number of writhing responses. **p<0.01 compared to vehicle control (dose=0) by one-way ANOVA.

A separate study was carried out to assess the use of 5-hydroxy-7-methyloxindole and acetaminophen in a 6% Tween® 20 vehicle (the vehicle needed for the safety study which follows. The two highest doses of acetaminophen were re-tested using vehicle consisting of 6% Tween® 20 reagent. Only a 300 mg/kg dose produced significant inhibition of acetic acid-induced response, and the magnitude of response was less than the response that was obtained with the DMSO/Cremophor™ vehicle (FIG. 5). In contrast, when the two highest doses of 5-hydroxy-7-methyloxindole were tested using the 6% Tween® vehicle, the highest dose produced an effect comparable to that observed with the DMSO/Cremophor™ vehicle (FIG. 6).

Example 11: Safety Measurement

This example was performed to determine if acute liver toxicity results from oral administration of 5-hydroxy-7-methyloxindole (CaRafe Drug Innovation, LLC) compared to the known acute liver toxicity produced by acetaminophen.

A. Chemicals

Acetaminophen was acquired from Sigma-Aldrich Corp. (St. Louis, Mo., USA); 5-hydroxy-7-methyloxindole was provided by CaRafe Drug Innovation, LLC (Norristown, Pa., USA) in the form of a powder. Initially it was planned to dissolve both substances in saline, but it was found that 5-hydroxy-7-methyloxindole is not sufficiently soluble. Based on the efficacy testing performed at Drexel University, 5-hydroxy-7-methyloxindole was suspended in 6% Tween® 20 reagent with vortexing. This procedure provided a crude suspension, but it precipitated after some time, therefore vortexing was repeated prior to each injection. Acetaminophen was prepared in the same vehicle (6% Tween® 20 reagent) using light magnetic stirring.

B. Animals

Ten-week old male C57BL/6 mice were used in all of the experiments. All protocols were approved before study initiation by the Ethics Committee of University of Zagreb School of Medicine (Zagreb, Croatia) and the study was conducted in accordance with accepted standards of humane animal care.

C. Experimental Design

In all experiments, mice were fasted overnight and then allocated randomly to receive either acetaminophen or equimolar dose of 5-hydroxy-7-methyloxindole by the intragastric route. Food was returned 4 h after the treatment. The two experimental groups were:

(a) Lower-dose group: Mice were administered acetaminophen (300 mg/kg) or 5-hydroxy-7-methyloxindole (324 mg/kg). After 7 h, the mice were sacrificed and liver and blood samples were taken for the analysis.

(b) Higher-dose group: Because of the low solubility of 5-hydroxy-7-methyloxindole, a higher dose of both substances was administered in two cumulative injections separated by 2.5 h, i.e., mice received intragastrically a total dose of 500 mg/kg of acetaminophen in two 250 mg/kg applications, or a total dose of 540 mg/kg of 5-hydroxy-7-methyloxindole in two 270 mg/kg applications. Seven hours after receiving the second injection, mice were sacrificed and liver and blood samples were taken for analysis.

D. Plasma Aminotransferase Activity

After collection, the blood samples were centrifuged, and plasma was separated and stored at −80° C. for 24 h. Activities of ALT (alanine transaminase) and of AST (aspartate transaminase) in plasma were determined using standard laboratory techniques in a clinical diagnostic laboratory.

E. Liver Histology

A portion of the liver lobes of each mouse was fixed in 4% buffered paraformaldehyde, dehydrated in increasing concentrations of ethanol, and embedded in paraffin. Then, sections of tissue were cut to 5 mm thickness using a rotary microtome, stained with hematoxylin and eosin, and then analyzed under a microscope.

F. Results (i) Lower-Dose Protocol

Treatment of mice with acetaminophen at the dose of 300 mg/kg resulted in significant liver damage, as evidenced by elevated levels of ALT and AST (Table 1). ALT and AST values were determined 7 h after the treatment. Levels of ALT in untreated animals were 15-40 U/L. Levels of AST in untreated animals were 40-80 U/L.

TABLE 1

ALT and AST levels of mice treated with 300 mg/kg of acetaminophen or an equimolar dose of 5-hydroxy-7-methyloxindole (324 mg/kg)

| | ALT (U/L) | | AST (U/L) | |
|---|---|---|---|---|
| Treatment | APAP (300 mg/kg) | 5-hydroxy-7-methyloxindole (324 mg/kg) | APAP (300 mg/kg) | 5-hydroxy-7-methyloxindole (324 mg/kg) |
| 1 | 3060 | 30 | 6090 | 80 |
| 2 | 7800 | 20 | 13500 | 80 |
| 3 | 1860 | 30 | 4050 | 60 |
| 4 | 2010 | 30 | 2098 | 120 |
| 5 | 11420 | 50 | 11180 | 330 |
| 6 | 6320 | 30 | 9220 | 60 |
| 7 | 8740 | 50 | 9990 | 170 |
| 8 | 13350 | 30 | 13770 | 90 |
| Mean | 6820 | 34 | 8737 | 124 |
| S.D. | 4319 | 11 | 4290 | 91 |

The presence of central liver necrosis was also confirmed pathohistologically. In contrast, ALT and AST values of mice treated with 5-hydroxy-7-methyloxindole were normal or only minimally elevated (Table 1) and there was no visible sign of liver injury on pathohistological examination.

(ii) Higher-Dose Protocol

Acetaminophen and 5-hydroxy-7-methyloxindole were injected in two cumulative injections separated by 2.5 h. Treatment of mice with acetaminophen at 540 mg/kg caused acute liver injury in all of the mice, as evidenced by both highly elevated levels of ALT and AST (Table 1) and by pathohistological findings. In contrast, mice treated with 5-hydroxy-7-methyloxindole (540 mg/kg) had normal or only minimally elevated levels of ALT and AST without visible liver injury on examination of pathohistological sections. ALT and AST values were determined 7 h after the second injections. Levels of ALT in untreated animals were 15-40 U/L and levels of AST in untreated animals were 40-80 U/L.

TABLE 2

ALT and AST levels of mice treated with 500 mg/kg of acetaminophen (APAP) or equimolar dose of 5-hydroxy-7-methyloxindole (324 mg/kg)

| | ALT | | AST | |
|---|---|---|---|---|
| Group | APAP (500 mg/kg) | 5-hydroxy-7-methyloxindole (540 mg/kg) | APAP (500 mg/kg) | 5-hydroxy-7-methyloxindole (540 mg/kg) |
| 1 | 7200 | 20 | 6700 | 60 |
| 2 | 13800 | 30 | 14200 | 120 |
| 3 | 10800 | 30 | 12300 | 120 |
| 4 | 12500 | 20 | 13100 | 100 |
| 5 | 11900 | 20 | 15200 | 60 |
| 6 | 13600 | 50 | 14700 | 120 |
| 7 | 14700 | 30 | 17000 | 70 |
| 8 | 11200 | 50 | 12800 | 110 |
| Mean | 11962.5 | 31.25 | 13250 | 95 |
| S.D. | 2343 | 12.5 | 3044.9 | 27.3 |

G. Analysis

5-Hydroxy-7-methyloxindole had significantly less hepatotoxicity than acetaminophen. A possible caveat is that 5-hydroxy-7-methyloxindole has low solubility, however the study followed the same protocol provided by Drexel University (efficacy study) that showed that 5-hydroxy-7-methyloxindole can be safely and efficiently administered intragastrically if suspended in Tween® 20 reagent with vortexing.

H. Summary

In a standard animal (mouse) model, 5-hydroxy-7-methyloxindole produced an oral antinociceptive (analgesic) effect (efficacy) that was equal to, and was slightly more potent than, acetaminophen. However, in distinct contrast to acetaminophen, 5-hydroxy-7-methyloxindole was devoid of hepatotoxic effect, as assessed by ALT (alanine transaminase) and AST (aspartate transaminase) assays and pathohistological examination.

Example 12: Receptor Binding of 5-hydroxy-7-methyloxindole

This example was performed to evaluate the binding of 5-hydroxy-7-methyloxindole on the opioid receptor and COX-1 and COX-2 receptors.

A. Opioid Receptor Binding Assay

The non-selective assay was performed according to the procedure described in Childers, European Journal of Pharmacology, 55:11-18, 1979, which is incorporated by reference. In summary, adult Male Sprague-Dawley rats were killed by decapitation and the brains rapidly removed and placed in ice-cold buffer. The cerebral cortex was dissected and homogenized in buffer and the homogenates were further centrifuged. The binding experiments were performed at 25° C. for 40 min. Reaction mixtures contained tissue suspension, unlabeled drug and [$^3$H]-naloxone (1 nM) radioligand.

B. Enzyme Assay

The assay was performed according to the procedure described in Glaser, European Journal of Pharmacology, 281:107-111, 1995, which is incorporated by reference. Recombinant enzymes were reconstituted in buffer. The enzyme preparations were preincubated with DMSO vehicle or compounds in DMSO for 5 min at 37° C. and the human recombinant enzyme expressed in Sf9 cells.

C. Results

An inhibition greater than about 50% represented significant effects of the test compound. An inhibition of about 25% to about 50% was indicative of weak to moderate effects. An inhibition less than about 25% are not considered significant and may be primarily attributable to variability of the signal around the control level. The results are shown in Table 3 and illustrate that 5-hydroxy-7-methyloxindole binds minimally, if at all, to the opioid, COX1 and COX2 receptors.

TABLE 3

| Receptor | Test concentration (M) | Mean Inhibition (%) |
|---|---|---|
| Opioid | $1 \times 10^{-5}$ | −9.7 |
| COX1 (h) | $1 \times 10^{-5}$ | −29.0 |
| COX2 (h) | $1 \times 10^{-5}$ | −6.8 |

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for treating pain or fever, comprising administering a compound of formula (I) to a subject, wherein said compound is:

wherein:
R$^1$ and R$^2$ are, independently, H, optionally substituted C$_1$ to C$_6$ alkyl, optionally substituted C$_3$ to C$_8$ cycloalkyl, optionally substituted C$_3$ to C$_8$ oxycycloalkyl, optionally substituted C$_1$ to C$_6$ hydroxyalkyl, NH$_2$, optionally substituted C$_1$ to C$_6$ alkylamino, optionally substituted C$_1$ to C$_6$ dialkylamino, OH, optionally substituted C$_1$ to C$_6$ alkoxy, optionally substituted C$_1$ to C$_6$ alkylcarboxy, optionally substituted C$_1$ to C$_3$ alkylidenecarboxy, optionally substituted C$_1$ to C$_6$ carbalkoxy, optionally substituted C$_1$ to C$_6$ alkylcarboxamido, N-(optionally substituted C$_1$ to C$_6$ alkyl)carboxamido, N,N-di(optionally substituted C$_1$ to C$_6$ alkyl)carboxamido, or optionally substituted C$_1$ to C$_6$ acyl; or
R$^1$ and R$^2$ are joined to form a 3 to 7 membered ring;

R$^3$ is H, optionally substituted C$_1$ to C$_6$ alkyl, optionally substituted C$_1$ to C$_6$ acyl, N,N-(di-optionally substituted C$_1$ to C$_6$ alkyl)aminoacyl), optionally substituted C$_1$ to C$_6$ carbalkoxy, optionally substituted C$_1$ to C$_3$ phosphatoalkylenyl, or optionally substituted C$_1$ to C$_3$ acyloxyalkylenyl;

R$^4$ is H, optionally substituted C$_1$ to C$_6$ alkyl, optionally substituted C$_1$ to C$_6$ acyl, N,N-(di-optionally substituted C$_1$ to C$_6$ alkyl)aminoacyl, N-(optionally substituted C$_1$ to C$_6$ alkyl)aminoacyl, C$_1$ to C$_6$ optionally substituted carbalkoxy, optionally substituted C$_1$ to C$_3$ phosphatoalkylenyl, amino(C$_3$ to C$_8$ optionally substituted cycloalkyl)acyl, or optionally substituted C$_1$ to C$_3$ acyloxyalkylenyl;

X, Y and Z are, independently, H, deuterium, optionally substituted C$_1$ to C$_6$ alkyl, optionally substituted C$_3$ to C$_8$ cycloalkyl, optionally substituted C$_1$ to C$_6$ hydroxyalkyl, optionally substituted C$_1$ to C$_6$ acyl, CN, halogen, C$_1$ to C$_3$ polyfluoroalkyl, NO$_2$, NH$_2$, optionally substituted C$_1$ to C$_6$ alkylamino, optionally substituted C$_1$ to C$_6$ dialkylamino, formyl, optionally substituted C$_1$ to C$_6$ carboxy, optionally substituted C$_1$ to C$_6$ carbalkoxy, OH, optionally substituted C$_1$ to C$_6$ alkoxy, or optionally substituted C$_1$ to C$_6$ thioalkoxy; or any two of X, Y, and Z are joined to form a 3 to 7 membered ring;
wherein R$^1$-R$^3$, X, Y, and Z are not all H;
or a pharmaceutically acceptable salt, solvate, or prodrug thereof.

2. The method of claim 1, wherein R$^3$ is H, Y is H, or Z is H.

3. The method of claim 1, wherein X is C$_1$ to C$_6$ alkyl.

4. The method of claim 1, wherein R$^4$ is H.

5. The method of claim 1, wherein X, Y and Z are not all H.

6. The method of claim 1, wherein said compound is 5-hydroxy-7-methyloxindole.

7. The method of claim 1, which does not result in liver-related side effects in said subject.

8. The method of claim 1, which does not display opioid side effects in said subject.

9. The method of claim 8, wherein said opioid side effect is physical drug dependence, constipation, CNS, or a combination thereof.

10. The method of claim 7, which does not display non-steroidal anti-inflammatory drug (NSAID) side effects in said subject.

11. The method of claim 10, wherein said NSAID side effect is gastrointestinal irritation, cardiovascular effects, or combinations thereof.

12. The method of claim 1, which does not function through the COX-1 receptor, COX-2 receptor, or any combinations thereof.

13. The method of claim 1, which does not damage the liver in said subject.

14. The method of claim 1, wherein a toxic metabolite analogous to the toxic metabolite produced by high doses of acetaminophen is not formed in said subject.

15. The method of claim 1, wherein the compound is at least about 3 times more potent than acetaminophen.

16. A composition comprising:
(a) one or more pharmaceutically acceptable excipient; and
(b) about 1000 mg or less of a compound of the structure of formula (I):

wherein:
R$^1$ and R$^2$ are, independently, H, optionally substituted C$_1$ to C$_6$ alkyl, optionally substituted C$_3$ to C$_8$ cycloalkyl, optionally substituted C$_3$ to C$_8$ oxycycloalkyl, optionally substituted C$_1$ to C$_6$ hydroxyalkyl, NH$_2$, optionally substituted C$_1$ to C$_6$ alkylamino, optionally substituted C$_1$ to C$_6$ dialkylamino, OH, optionally substituted C$_1$ to C$_6$ alkoxy, optionally substituted C$_1$ to C$_6$ alkylcarboxy, optionally substituted C$_1$ to C$_3$ alkylidenecarboxy, optionally substituted C$_1$ to C$_6$ carbalkoxy, optionally substituted C$_1$ to C$_6$ alkylcarboxamido, N-(optionally substituted C$_1$ to C$_6$ alkyl)carboxamido, N,N-di(optionally substituted C$_1$ to C$_6$ alkyl)carboxamido, or optionally substituted C$_1$ to C$_6$ acyl; or R$^1$ and R$^2$ are joined to form a 3 to 7 membered ring;

R$^3$ is H, optionally substituted C$_1$ to C$_6$ alkyl, optionally substituted C$_1$ to C$_6$ acyl, N,N-(di-optionally substituted C$_1$ to C$_6$ alkyl)aminoacyl), optionally substituted C$_1$ to C$_6$ carbalkoxy, optionally substituted C$_1$ to C$_3$ phosphatoalkylenyl, or optionally substituted C$_1$ to C$_3$ acyloxyalkylenyl;

R$^4$ is H, optionally substituted C$_1$ to C$_6$ alkyl, optionally substituted C$_1$ to C$_6$ acyl, N,N-(di-optionally substituted C$_1$ to C$_6$ alkyl)aminoacyl, N-(optionally substituted C$_1$ to C$_6$ alkyl)aminoacyl, C$_1$ to C$_6$ optionally substituted carbalkoxy, optionally substituted C$_1$ to C$_3$ phosphatoalkylenyl, amino(C$_3$ to C$_8$ optionally substituted cycloalkyl)acyl, or optionally substituted C$_1$ to C$_3$ acyloxyalkylenyl;

X, Y and Z are, independently, H, optionally substituted C$_1$ to C$_6$ alkyl, optionally substituted C$_3$ to C$_8$ cycloalkyl, optionally substituted C$_1$ to C$_6$ hydroxyalkyl, optionally substituted C$_1$ to C$_6$ acyl, CN, halogen, C$_1$ to C$_3$ polyfluoroalkyl, NO$_2$, NH$_2$, optionally substituted C$_1$ to C$_6$ alkylamino, optionally substituted C$_1$ to C$_6$ dialkylamino, formyl, optionally substituted C$_1$ to C$_6$ carboxy, optionally substituted C$_1$ to C$_6$ carbalkoxy, OH, optionally substituted C$_1$ to C$_6$ alkoxy, or optionally substituted C$_1$ to C$_6$ thioalkoxy; or any two of X, Y, and Z are joined to form a 3 to 7 membered ring;

wherein R$^1$-R$^3$, X, Y, and Z are not all H;

or a pharmaceutically acceptable salt, solvate, or prodrug thereof.

17. The composition of claim 16, wherein said excipient is a polyethylene glycol, polyvinylpyrrolidone, PEG-8 caprylic/capric glycerides, cyclodextrin, polysorbate, carboxymethylcellulose, hydroxypropylcellulose, or any combinations thereof.

18. The composition of claim 16, further comprising an opiate.

19. The composition of claim 18, wherein said opioid is the alkaloids contained in the resin of the opium poppy, codeine, thebaine, leaves from *Mitragyna speciosa*, Salvinorin A, diacetylmorphine, nicomorphine, dipropanoylmorphine, desomorphine, acetylpropionylmorphine, dibenzoylmorphine, diacetyldihydromorphine, hydromorphone, hydrocodone, oxycodone, oxymorphone, ethylmorphine buprenorphine, fentanyl, pethidine, levorphanol, methadone, tramadol dextropropoxyphene, endorphins, enkephalins, dynorphins, endomorphins, morphine, or any combinations thereof.

20. A kit comprising:
(a) about 1000 mg or less of a compound of the structure of formula (I):

wherein:
R$^1$ and R$^2$ are, independently, H, optionally substituted C$_1$ to C$_6$ alkyl, optionally substituted C$_3$ to C$_8$ cycloalkyl, optionally substituted C$_3$ to C$_8$ oxycycloalkyl, optionally substituted C$_1$ to C$_6$ hydroxyalkyl, NH$_2$, optionally substituted C$_1$ to C$_6$ alkylamino, optionally substituted C$_1$ to C$_6$ dialkylamino, OH, optionally substituted C$_1$ to C$_6$ alkoxy, optionally substituted C$_1$ to C$_6$ alkylcarboxy, optionally substituted C$_1$ to C$_3$ alkylidenecarboxy, optionally substituted C$_1$ to C$_6$ carbalkoxy, optionally substituted C$_1$ to C$_6$ alkylcarboxamido, N-(optionally substituted C$_1$ to C$_6$ alkyl)carboxamido, N,N-di(optionally substituted C$_1$ to C$_6$ alkyl)carboxamido, or optionally substituted C$_1$ to C$_6$ acyl; or R$^1$ and R$^2$ are joined to form a 3 to 7 membered ring;

R$^3$ is H, optionally substituted C$_1$ to C$_6$ alkyl, optionally substituted C$_1$ to C$_6$ acyl, N,N-(di-optionally substituted C$_1$ to C$_6$ alkyl)aminoacyl), optionally substituted C$_1$ to C$_6$ carbalkoxy, optionally substituted C$_1$ to C$_3$ phosphatoalkylenyl, or optionally substituted C$_1$ to C$_3$ acyloxyalkylenyl;

R$^4$ is H, optionally substituted C$_1$ to C$_6$ alkyl, optionally substituted C$_1$ to C$_6$ acyl, N,N-(di-optionally substituted C$_1$ to C$_6$ alkyl)aminoacyl, N-(optionally substituted C$_1$ to C$_6$ alkyl)aminoacyl, C$_1$ to C$_6$ optionally substituted carbalkoxy, optionally substituted C$_1$ to C$_3$ phosphatoalkylenyl, amino(C$_3$ to C$_8$ optionally substituted cycloalkyl)acyl, or optionally substituted C$_1$ to C$_3$ acyloxyalkylenyl;

X, Y and Z are, independently, H, optionally substituted C$_1$ to C$_6$ alkyl, optionally substituted C$_3$ to C$_8$ cycloalkyl, optionally substituted C$_1$ to C$_6$ hydroxyalkyl, optionally substituted C$_1$ to C$_6$ acyl, CN, halogen, C$_1$ to C$_3$ polyfluoroalkyl, NO$_2$, NH$_2$, optionally substituted C$_1$ to C$_6$ alkylamino, optionally substituted C$_1$ to C$_6$ dialkylamino, formyl, optionally substituted C$_1$ to C$_6$ carboxy, optionally substituted C$_1$ to C$_6$ carbalkoxy, OH, optionally substituted C$_1$ to C$_6$ alkoxy, or optionally substituted C$_1$ to C$_6$ thioalkoxy; or any two of X, Y, and Z are joined to form a 3 to 7 membered ring;

wherein R$^1$-R$^3$, X, Y, and Z are not all H;

or a pharmaceutically acceptable salt, solvate, or prodrug thereof; and (b) instructions for administering said compound to a subject.

21. The kit of claim 20, further comprising an opiate.

22. The kit of claim 21, wherein said opioid is the alkaloids contained in the resin of the opium poppy, codeine, thebaine, leaves from *Mitragyna speciosa*, Salvinorin A, diacetylmorphine, nicomorphine, dipropanoylmorphine, desomorphine, acetylpropionylmorphine, dibenzoylmorphine, diacetyldihydromorphine, hydromorphone, hydrocodone, oxycodone, oxymorphone, ethylmorphine buprenorphine, fentanyl, pethidine, levorphanol, methadone, tramadol dextropropoxyphene, endorphins, enkephalins, dynorphins, endomorphins, morphine, or any combinations thereof.

\* \* \* \* \*